US008298530B2

(12) United States Patent
Kaisheva et al.

(10) Patent No.: US 8,298,530 B2
(45) Date of Patent: *Oct. 30, 2012

(54) STABLE LYOPHILIZED PHARMACEUTICAL FORMULATION OF IGG ANTIBODIES

(75) Inventors: Elizabet A. Kaisheva, Belmont, CA (US); Aleni Flores-Nate, Union City, CA (US); Supriya Gupta, Sunnyvale, CA (US)

(73) Assignee: Facet Biotech Corporation, Redwood City, CA (US)

( * ) Notice: Subject to any disclaimer, the term of this patent is extended or adjusted under 35 U.S.C. 154(b) by 113 days.

This patent is subject to a terminal disclaimer.

(21) Appl. No.: 12/540,320

(22) Filed: Aug. 12, 2009

(65) Prior Publication Data

US 2010/0055097 A1 Mar. 4, 2010

Related U.S. Application Data

(63) Continuation of application No. 11/250,835, filed on Oct. 14, 2005, now Pat. No. 7,592,004, which is a continuation of application No. 10/206,469, filed on Jul. 25, 2002, now abandoned.

(60) Provisional application No. 60/307,878, filed on Jul. 25, 2001.

(51) Int. Cl.
A61K 39/395 (2006.01)
(52) U.S. Cl. ............... 424/130.1; 424/141.1; 424/144.1
(58) Field of Classification Search .................. None
See application file for complete search history.

(56) References Cited

U.S. PATENT DOCUMENTS

| | | | |
|---|---|---|---|
| 4,618,486 | A | 10/1986 | Lundblad |
| 5,091,178 | A | 2/1992 | Hellstrom et al. |
| 5,268,368 | A | 12/1993 | Palepu |
| 5,334,380 | A | 8/1994 | Kilbourn et al. |
| 5,677,171 | A | 10/1997 | Hudziak et al. |
| 5,714,477 | A | 2/1998 | Einarsson |
| 5,780,054 | A | 7/1998 | Tardi et al. |
| 5,783,592 | A | 7/1998 | Schwartz et al. |
| 5,792,753 | A | 8/1998 | Falk et al. |
| 5,824,658 | A | 10/1998 | Falk et al. |
| 5,827,818 | A | 10/1998 | Eibl et al. |
| 6,171,586 | B1 | 1/2001 | Lam et al. |
| 6,267,958 | B1 | 7/2001 | Andya et al. |
| 6,685,940 | B2 | 2/2004 | Andya et al. |
| 7,132,100 | B2 | 11/2006 | Oliver et al. |
| 7,592,004 | B2 | 9/2009 | Kaisheva et al. |
| 2006/0034827 | A1 | 2/2006 | Oliver et al. |

FOREIGN PATENT DOCUMENTS

| | | |
|---|---|---|
| EP | 0271918 A2 | 6/1988 |
| WO | 89/11297 A1 | 11/1989 |
| WO | 97/04801 A1 | 2/1997 |
| WO | 97/45140 A1 | 12/1997 |
| WO | 98/56418 A1 | 12/1998 |

OTHER PUBLICATIONS

Vincenti et al. N. Eng. J. Med, 1998 vol. 338 p. 161-165.*
Belliveau, Paul P. "Omalizumab: a monoclonal anti-IgE antibody." MedGenMed. Jan. 27, 2005;7(1):27.
Cleland, Jeffrey L. et al. "A specific molar ratio of stabilizer to protein is required for storage stability of a lyophilized monoclonal antibody." J Pharm Sci. Mar. 2001;90(3):310-21.
Daugherty, Ann L. et al. "Formulation and delivery issues for monoclonal antibody therapeutics." Adv Drug Deliv Rev. Aug. 7, 2006;58(5-6):686-706.
Patro, Sugunakar Y. et al. "Protein formulation and fill-finish operations." Biotechnol Annu Rev. 2002;8:55-84.
Wang, Wei. "Instability, stabilization, and formulation of liquid protein pharmaceuticals." Int J Pharm. Aug. 20, 1999;185(2):129-88.
Wang, Wei. "Lyophilization and development of solid protein pharmaceuticals." Int J Pharm. Aug. 10, 2000;203(1-2):1-60.
"Synagis Intramuscular (Medimmune)." Physician's Desk Reference pp. 1-4 (2001).
Xolair package insert, p. 1-4, 2003.
Zenapax Product Information, Roche, 1999, p. 1-11.
Zenapax Product Information Sheet, 2003, p. 1-10.
Non-Final Office Action for U.S. Appl. No. 10/206,469, mailed on Dec. 16, 2004; pp. 4.
Non-Final Office Action for U.S. Appl. No. 10/206,469, mailed on Apr. 18, 2005; pp. 6.
Non-Final Office Action for U.S. Appl. No. 11/250,835, mailed on Jan. 30, 2008; pp. 4.
Non-Final Office Action for U.S. Appl. No. 11/250,835, mailed on Oct. 10, 2006; pp. 6.
Final Office Action for U.S. Appl. No. 11/250,835, mailed on Jun. 1, 2007; pp. 6.
Non-Final Office Action for U.S. Appl. No. 11/250,835, mailed on Jun. 16, 2008; pp. 10.
Interview Summary of Oct. 2, 2008 regarding U.S. Appl. No. 11/250,835, mailed on Oct. 7, 2008; pp. 2.
Final Office Action for U.S. Appl. No. 11/250,835, mailed on Jan. 2, 2009; pp. 4.
Notice of Allowance and Fee(s) Due for U.S. Appl. No. 11/250,835, mailed on May 14, 2009; pp. 7.
European Supplementary Search Report for application EP02759206 mailed Feb. 27, 2007.
PCT Search Report for application PCT/US2002/024078 mailed Aug. 7, 2003.

* cited by examiner

Primary Examiner — Yunsoo Kim
(74) Attorney, Agent, or Firm — Alston & Bird LLP

(57) ABSTRACT

This invention is directed to a stable lyophilized pharmaceutical formulation prepared by lyophilizing an aqueous formulation comprising a high concentration, e.g. 50 mg/ml or more, of an IgG antibody in about 5-25 mM histidine buffer having pH from about 5.5 to about 6.5, about 0.005%-0.03% polysorbate, sucrose, and optionally serine, and/or mannitol. This lyophilized formulation is stable at room temperature for at least 6 months, and preferably 1 year. This lyophilized formulation has a short reconstitution time of less than 2 minutes, and is suitable for parenteral administration such as intravenous, intramuscular, intraperitoneal, or subcutaneous injection. This invention is exemplified by the anti-IL2 receptor antibody.

9 Claims, 11 Drawing Sheets

STABLE LYOPHILIZED PHARMACEUTICAL FORMULATION OF IGG ANTIBODIES

This application is a continuation of U.S. application Ser. No. 11/250,835, filed Oct. 14, 2005 (now U.S. Pat. No. 7,592, 004); which is a continuation of U.S. application Ser. No. 10/206,469, filed Jul. 25, 2002 now abandoned; which claims the benefit of U.S. Provisional Application No. 60/307,878, filed Jul. 25, 2001. The contents of each of these applications are incorporated herein by reference in their entirety.

FIELD OF THE INVENTION

The present invention relates generally to the field of pharmaceutical formulation of antibodies. Specifically, the present invention relates to a stable, lyophilized, high concentration antibody formulation. This invention is exemplified by a stabilized lyophilized formulation of anti-$IL_2$ receptor antibody.

BACKGROUND OF THE INVENTION

It is well known that many protein preparations intended for administration to humans require stabilizers to prevent denaturation, aggregation and other alternations to the proteins prior to the use of the preparation. Many protein preparations are particularly unstable in very dilute or highly concentrated solutions. This instability is manifested in the formation of soluble/insoluble aggregates, and is often increased when the protein preparation is stored, or shipped. A major challenge that exists in the field of protein drugs is in the development of formulations that maintain both protein stability and activity.

Immunoglobulins, in particular, are recognized as possessing characteristics that tend to form aggregates and particulates in solution; thus requiring filtration of these formulations prior to using them for intravenous injection. The formation of protein aggregates and particulates has long been a problem in the development of parenteral immunoglobulin products. There is a need in the art for a stable pharmaceutical formulation comprising an antibody.

WO 89/11297 discloses a lyophilized composition comprising a monoclonal immunoglobulin antibody of 1-25 mg/ml, 2-10% maltose, and sodium acetate, phosphate, or citrate buffer having a pH between 3.0 to 6.0.

Synagis™ (MedImmune) is a humanized monoclonal IgG1 antibody produced by recombinant DNA technology, directed to an epitope in the A antigenic site of the T protein of respiratory syncytial virus (RSV). Synagis™ is a composite of human (95%) and murine (5%) antibody sequences. Synagis™ is supplied as a sterile lyophilized product for reconstitution with sterile water for injection. Reconstituted Synagis™ is required to stand at room temperature for a minimum of 20 minutes until the solution clarifies. Reconstituted Synagis™ is to be administered by intramuscular injection only. Upon reconstitution, Synagis™ contains the following excipients: 47 mM histidine, 3.0 mM glycine and 5.6% mannitol and the active ingredient, IgG1 antibody, at a concentration of 100 milligrams per vial. (See Physicians' Desk Reference®, Medical Economic Company, Inc., Montvale, N.J.)

U.S. Patent Application Publication No. US 2001/0014326A1 discloses a pre-lyophilized antibody formulation containing 25 mg/ml anti-IgE antibody, 5 mM histidine, pH 6.0, 85 mM sucrose, and 0.01% polysorbate 20.

U.S. Pat. No. 6,171,586 discloses a stable aqueous pharmaceutical formulation comprising a therapeutically effective amount of an antibody not subjected to prior lyophilization, and acetate buffer from about pH 4.8 to about 5.5, a surfactant, and a polyol, wherein the formulation lacks a tonicifying amount of sodium chloride.

WO 97/45140 discloses a monoclonal antibody preparation of a humanized antibody against the CDw52 antigen, having a concentration of 100 mg/ml or greater, wherein the preparation is substantially free from aggregates.

Cleland, et al. (*J. Pharm. Sci.*, 90:310-321 (2001)) disclose that a 360:1 molar ratio of lyoprotectant to protein is required for storage stability of a lyophilized monoclonal antibody.

There is a need for a stable, highly concentrated lyophilized antibody preparation for administration to a human, such antibody can be reconstituted within a short time and is suitable for parenteral administration, including intravenous, intramuscular, intraperitoneal, or subcutaneous injection.

SUMMARY OF THE INVENTION

This invention is directed to a stable lyophilized pharmaceutical formulation prepared from an aqueous formulation comprising a high concentration, e.g., greater than 50 mg/ml of an IgG antibody in about 5-25 mM histidine buffer (pH from about 5.5 to about 6.5), about 0.005%-0.03% polysorbate, and sucrose, optionally in combination with serine, and/or mannitol. This formulation retains the stability of the IgG antibody, and prevents the immunoglobulins intended for administration to human subjects from forming aggregates/particulates in the final product. The lyophilized formulation is reconstituted with a liquid to a clarified solution containing greater than 50 mg/ml IgG antibody concentration within about 2 minutes or less.

This lyophilized formulation is stable at room temperature for at least 3 months, preferably 6 months, and more preferably 1 year. The lyophilized formulation is also stable at 2-8° C. for 1 year, preferably 2 years. This lyophilized formulation has a short reconstitution time of less than 2 minutes, and is suitable for parenteral administration such as intravenous, intramuscular, intraperitoneal, or subcutaneous injection.

BRIEF DESCRIPTION OF THE FIGURES

FIG. 2A shows the % drop in monomer. FIG. 2B shows the reconstruction time.

FIG. 3A shows the % drop in monomer. FIG. 3B shows the reconstitution time.

FIG. 5A shows the % monomer drop. FIG. 5B shows the reconstitution time.

FIG. 6A shows the % monomer drop. FIG. 6B shows the reconstitution time.

FIG. 7A shows the % monomer drop. FIG. 7B shows the reconstitution time.

FIG. 8A shows the % monomer drop. FIG. 8B shows the reconstitution time.

DETAILED DESCRIPTION OF THE INVENTION

Figure 1A:
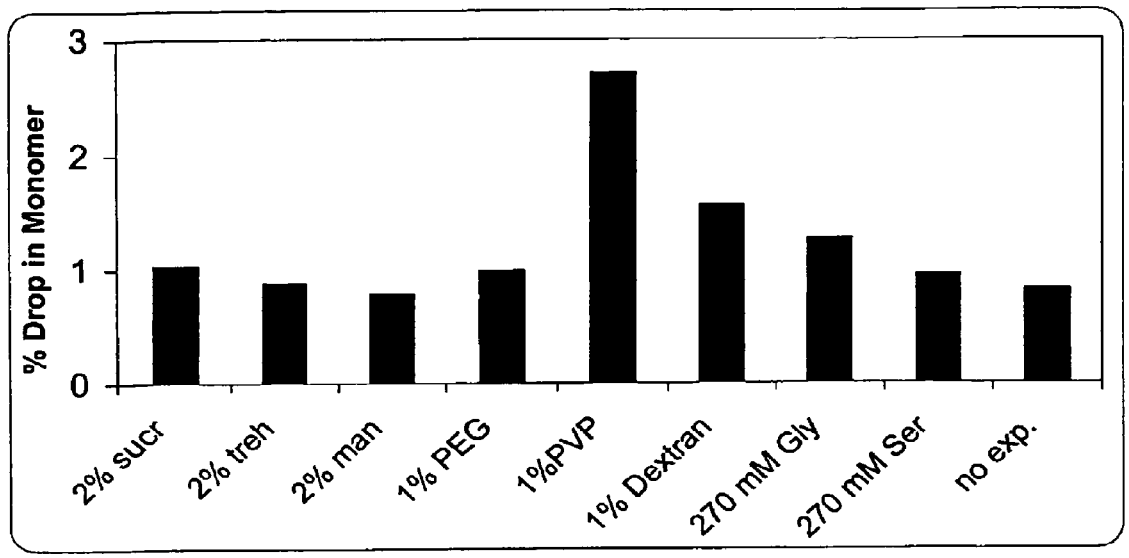
FIG. 1 shows the effect of excipients on antibody stability by testing (A) the liquid after storage at 55° C. for 10 days and (B) the lyophile at 40° C. for 12 days.

It is an object of the present invention to provide a lyophilized highly concentrated antibody formulation that is stable upon storage and delivery. It is a further object to provide a lyophilized highly concentrated antibody formulation that can be reconstituted in a short time prior to administration to a patient.

I. Definition

The term "bulking agents" comprise agents that provide the structure of the freeze-dried product. Common examples used for bulking agents include mannitol, glycine, lactose and sucrose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers.

The term "buffer" encompasses those agents which maintain the solution pH in an acceptable range prior to lyophilization and may include succinate (sodium or potassium), histidine, phosphate (sodium or potassium), Tris (tris (hydroxymethyl) aminomethane), diethanolamine, citrate (sodium) and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "cryoprotectants" generally includes agents which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as sucrose, glucose, trehalose, and lactose; surfactants such as polysorbates; and amino acids such as glycine, arginine, and serine.

The terms "lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

The term "lyoprotectant" includes agents that provide stability to the protein during the drying or 'dehydration' process (primary and secondary drying cycles), presumably by providing an amorphous glassy matrix and by binding with the protein through hydrogen bonding, replacing the water molecules that are removed during the drying process. This helps to maintain the protein conformation, minimize protein degradation during the lyophilization cycle and improve the long-term product stability. Examples include polyols or sugars such as sucrose and trehalose.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the time that is required to rehydrate a lyophilized formulation with a solution to a particle-free clarified solution.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. Adv. Drug Delivery Rev. 10:29-90 (1993). Stability can be measured at a selected temperature for a selected time period.

A "stable" lyophilized antibody formulation is a lyophilized antibody formulation with no significant changes observed at a refrigerated temperature (2-8° C.) for at least 12 months, preferably 2 years, and more preferably 3 years; or at room temperature (23-27° C.) for at least 3 months, preferably 6 months, and more preferably 1 year. The criteria for stability are as follows. No more than 10%, preferably 5%, of antibody monomer is degraded as measured by SEC-HPLC. The rehydrated solution is colorless, or clear to slightly opalescent by visual analysis. The concentration, pH and osmolality of the formulation have no more than +/−10% change. Potency is within 70-130, preferably 80-120% of the control. No more than 10%, preferably 5% of clipping is observed. No more than 10%, preferably 5% of aggregation is formed.

An antibody "retains its physical stability" in a pharmaceutical formulation if it shows no significant increase of aggregation, precipitation and/or denaturation upon visual examination of color and/or clarity, or as measured by UV light scattering, size exclusion chromatography (SEC) and dynamic light scattering. The changes of protein conformation can be evaluated by fluorescence spectroscopy, which determines the protein tertiary structure, and by FTIR spectroscopy, which determines the protein secondary structure.

An antibody "retains its chemical stability" in a pharmaceutical formulation, if it shows no significant chemical alteration. Chemical stability can be assessed by detecting and quantifying chemically altered forms of the protein. Degradation processes that often alter the protein chemical structure include hydrolysis or clipping (evaluated by methods such as size exclusion chromatography and SDS-PAGE), oxidation (evaluated by methods such as by peptide mapping in conjunction with mass spectroscopy or MALDI/TOF/MS), deamidation (evaluated by methods such as ion-exchange chromatography, capillary isoelectric focusing, peptide mapping, isoaspartic acid measurement), and isomerization (evaluated by measuring the isoaspartic acid content, peptide mapping, etc.).

An antibody "retains its biological activity" in a pharmaceutical formulation, if the biological activity of the antibody at a given time is within a predetermined range of the biological activity exhibited at the time the pharmaceutical formulation was prepared. The biological activity of an antibody can be determined, for example, by an antigen binding assay.

The term "isotonic" means that the formulation of interest has essentially the same osmotic pressure as human blood. Isotonic formulations will generally have an osmotic pressure from about 270-328 mOsm. Slightly hypotonic pressure is 250-269 and slightly hypertonic pressure is 328-350 mOsm.

Osmotic pressure can be measured, for example, using a vapor pressure or ice-freezing type osmometer.

Tonicity Modifiers: Salts (NaCl, KCl, MgCl$_2$, CaCl$_2$, etc) are used as tonicity modifiers to control osmotic pressure. In addition, cryprotecants/lyoprotectants and/or bulking agents such as sucrose, mannitol, glycine etc. can serve as tonicity modifiers.

II. Analytical Methods

The analytical methods for evaluating the product stability include size exclusion chromatography (SEC), dynamic light scattering test (DLS), differential scanning calorimetery (DSC), iso-asp quantification, potency, UV at 340 nm, UV spectroscopy, and FTIR. SEC (*J. Pharm. Scien.*, 83:1645-1650, (1994); *Pharm. Res.*, 11:485 (1994); *J. Pharm. Bio. Anal.*, 15:1928 (1997); *J. Pharm. Bio. Anal.*, 14:1133-1140 (1986)) measures percent monomer in the product and gives information of the amount of soluble aggregates. DSC (*Pharm. Res.*, 15:200 (1998); *Pharm. Res.*, 9:109 (1982)) gives information of protein denaturation temperature and glass transition temperature. DLS (*American Lab.*, November (1991)) measures mean diffusion coefficient, and gives information of the amount of soluble and insoluble aggregates. UV at 340 nm measures scattered light intensity at 340 nm and gives information about the amounts of soluble and insoluble aggregates. UV spectroscopy measures absorbance at 278 nm and gives information of protein concentration. FTIR (*Eur. J. Pharm. Biopharm.*, 45:231 (1998); *Pharm. Res.*, 12:1250 (1995); *J. Pharm. Scien.*, 85:1290 (1996); *J. Pharm. Scien.*, 87:1069 (1998)) measures IR spectrum in the amide one region, and gives information of protein secondary structure.

The iso-asp content in the samples is measured using the Isoquant Isoaspartate Detection System (Promega). The kit uses the enzyme Protein Isoaspartyl Methyltransferase (PIMT) to specifically detect the presence of isoaspartic acid residues in a target protein. PIMT catalyzes the transfer of a methyl group from S-adenosyl-L-methionine to isoaspartic acid at the α-carboxyl position, generating S-adenosyl-L-homocysteine (SAH) in the process. This is a relatively small molecule, and can usually be isolated and quantitated by reverse phase HPLC using the SAH HPLC standards provided in the kit.

The potency or bioidentity of an antibody can be measured by its ability to bind to its antigen. The specific binding of an antibody to its antigen can be quantitated by any method known to those skilled in the art, for example, an immunoassay, such as ELISA (enzyme-linked immunosorbant assay).

III. Preparation of Antibody

The invention herein relates to a stable formulation comprising an antibody. The antibody is prepared using techniques available in the art for generating antibodies, exemplary methods of which are described in more detail in the following sections.

The antibody is directed against an antigen of interest. Preferably, the antigen is a biologically important polypeptide and administration of the antibody to a mammal may prevent or treat a disorder. However, antibodies directed against nonpolypeptide antigens (such as tumor-associated glycolipid antigens; see U.S. Pat. No. 5,091,178) are also contemplated.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-.beta.; platelet-derived growth factor (PDGF); fibroblast growth factor such as aFGF and bFGF; epidermal growth factor (EGF); transforming growth factor (TGF) such as TGF-α and TGF-β, including TGF-β$_1$, TGF-β$_2$, TGF-β$_3$, TGF-β$_4$, or TGF-β$_5$; insulin-like growth factor-I and -II (IGF-I and IGF-II); des(1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-α, -β, and -γ; colony stimulating factors (CSFs), e.g., M-CSF, GM-CSF, and G-CSF; interleukins (ILs), e.g., IL-1 to IL-10; receptors to interleukins IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides.

When using recombinant techniques, the antibody can be produced intracellularly, in the periplasmic space, or directly secreted into the medium. If the antibody is produced intracellularly, as a first step, the particulate debris, either host cells or lysed cells, is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ$_1$, γ$_2$, or γ$_4$ heavy chains (Lindmark et al., *J. Immunol. Meth.*

62:1-13 (1983)). Protein G is recommended for all mouse isotypes and for human $\gamma_3$ (Guss et al., *EMBO J.* 5:1567-1575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSET™ chromatography on an anion or cation exchange resin (such as a polyaspartic acid column), chromatofocusing, SDS-PAGE, and ammonium sulfate precipitation are also available depending on the antibody to be recovered.

A preferred antibody encompassed by the present invention is an IgG antibody. This invention is exemplified by an anti-IL-2 receptor antibody such as Daclizumab. Daclizumab is a recombinant humanized monoclonal antibody, subclass IgG1. The molecule is composed of two identical heavy chain and two identical light chain subunits. Disulfide bridges link the four chains. Daclizumab monomer is approximately 150,000 daltons in molecular weight. Daclizumab binds to the p55 subunit of the IL-2 receptor expressed on activated T cells. The antigen target is designated CD25. Daclizumab is produced from a GS-NS0 cell line containing the heavy and light chain genes by fed-batch fermentation culture. Bioreactor harvests are processed to remove cells and debris and purified using a combination of ion-exchange and gel filtration chromatography and a series of ultrafiltration and filtration techniques to produce drug substance containing greater than 95% monomeric species.

IV. Preparation of the Formulation

After the antibody of interest is prepared as described above, the pharmaceutical formulation comprising the antibody is prepared. The formulation development approach is as follows: selecting the optimum solution pH, selecting buffer type and concentration, evaluating the effect of various excipients of the liquid and lyophilized stability, and optimizing the concentration of the screened excipients using an I-optimal experimental design (Statistics for Experimental, Box, George E. P. John Wiley and Sons, Inc., 1978).

The following criteria are important in developing stable lyophilized protein products. Protein unfolding during lyophilization should be minimized. Various degradation pathways should be minimized. Glass transition temperature (Tg) should be greater than the product storage temperature. Residual moisture should be low (<1% by mass). A strong and elegant cake structure should be obtained. A preferred shelf life should be at least 3 months, preferably 6 months, more preferably 1 year at room temperature (22 to 28° C.). A reconstitution time should be short, for example, less than 5 minutes, preferably less than 2 minutes, and more preferably less than 1 minute. When the lyophilized product is reconstituted, the reconstituted sample should be stable for at least 48 hours at 2-8° C.

The compositions of this invention minimize the formation of protein aggregates and particulates in reagents containing immunoglobulin antibodies and insure that the antibody in solution maintains its immunoreactivity over time. The composition comprises a sterile, pharmaceutically acceptable lyophilized formulation prepared from an aqueous pre-lyophilized formulation comprising an antibody in a buffer having a neutral or acidic pH (pH 5.5-6.5), a surfactant, and a polyol. The preferred composition additionally contains a bulking agent, and/or a tonicity modifier.

The antibody in the pre-lyophilized formulation has a high concentration of 50 mg/ml or greater. A preferred antibody is an IgG antibody, preferably a monoclonal IgG antibody.

A buffer of pH 5.5-6.5 is used in the composition. Examples of buffers that control the pH in this range include succinate (such as sodium succinate), gluconate, histidine, citrate and other organic acid buffers. Histidine is a preferred buffer for subcutaneous, intramuscular and peritoneal injection. Sodium succinate buffer is less preferred because it does not have a good buffer capacity at low strength. To increase the buffer strength of sodium succinate, the amount of the excipients will have to be decreased in order to maintain the osmolarity in a desired range. If the lyophile is to be reconstituted with half of the fill volume, then the desired osmolarity of the pre-lyophilized (fill) liquid is about 140-160 mOsm. The advantage of histidine buffer is that 1 mmole of the histidine buffer only contributes 1 mOsm, whereas 1 mmole of the sodium succinate buffer contributes 3 mOsm. Because histidine buffer contributes less to the osmolarity, it allows more stabilizing excipients to be added to the formulation. Citrate buffer is also less preferred because it causes a painful reaction when injected subcutaneously. A preferred buffer contains about 5-25 mM histidine. A more preferred buffer contains about 10-20 mM histidine.

A surfactant is added to the antibody formulation. Exemplary surfactants include nonionic surfactants such as polysorbates (e.g. polysorbates 20, 80, such as Tween® 20, Tween® 80) or poloxamers (e.g. poloxamer 188). The amount of surfactant added is such that it reduces aggregation of the formulated antibody and/or minimizes the formation of particulates in the formulation and/or reduces protein adsorption onto the container. The surfactant also reduces the reconstitution time of the lyophilized formulation. For example, the surfactant is present in the formulation in an amount from about 0.001% to about 0.5%, preferably from about 0.005% to about 0.1% and most preferably from about 0.01% to about 0.05%.

A polyol, which acts as a tonicifying agent and a cryoprotector/lyoprotector, is included in the formulation. In a preferred embodiment, the polyol is a nonreducing sugar, such as sucrose or trehalose. In the present invention, the polyol such as sucrose is the primary stabilizer against antibody aggregation, and it also plays an important role in reducing the reconstitution time of the lyophilized formulation to a particle-free solution. The polyol is added to the formulation in an amount that may vary with respect to the desired tonicity of the formulation. Preferably the lyophilized formulation after reconstitution is isotonic; however, hypertonic or hypotonic formulations may also be suitable. Suitable concentrations of the polyol such as sucrose in the pre-lyophilized formulation are in the range from about 100-300 mM, preferably in the range from about 100-200 mM.

A bulking agent that provides good lyophilized cake properties, such as serine, glycine, mannitol, can be optionally added to the present composition. These agents also contribute to the tonicity of the formulations and may provide protection to the freeze-thaw process and improve long-term stability. A preferred bulking agent is serine at a concentration about 15-55 mM, and preferably about 20-30 mM. Another preferred bulking agent is mannitol, at a concentration about 10-55 mM, and preferably about 20-45 mM. The addition of serine or mannitol to the pre-lyophilized formulation reduces the concentration of polyol required for stabilizing the antibody, for example, to 30-180 mM and preferably 80-130 mM.

Tonicity modifiers such as salts (e.g., NaCl, KCl, $MgCl_2$, $CaCl_2$) can be added to the formulation to control osmotic pressure.

Exemplary pre-lyophilized compositions are formulations comprising an IgG antibody at about 50 mg/ml or greater, about 10-20 mM histidine (pH 5.5-6.5), about 0.005-0.03% polysorbate 20 or 80, and one of the following combinations of excipients: (a) 100-200 mM sucrose, (b) 110-130 mM sucrose and 20-45 mM mannitol, (c) 100-130 mM sucrose and 15-55 mM serine, and (d) 7-55 mM serine, 80-130 mM sucrose, and 10-55 mM mannitol. The above pre-lyophilized formulation is lyophilized to form a dry, stable powder, which can be easily reconstituted to a particle-free solution suitable for administering to humans.

Lyophilization is a freeze drying process that is often used in the preparation of pharmaceutical products to preserve their biological activity. The liquid composition is prepared, then lyophilized to form a dry cake-like product. The process generally involves drying a previously frozen sample in a vacuum to remove the ice, leaving the non-water components intact, in the form of a powdery or cake-like substance. The lyophilized product can be stored for prolonged periods of time, and at elevated temperatures, without loss of biological activity, and can be readily reconstituted into a particle-free solution by the addition of an appropriate diluent. An appropriate diluent can be any liquid which is biologically acceptable and in which the lyophilized powder is completely soluble. Water, particularly sterile, pyrogen-free water, is a preferred diluent, since it does not include salts or other compounds which may affect the stability of the antibody. The advantage of lyophilization is that the water content is reduced to a level that greatly reduce the various molecular events which lead to instability of the product upon long-term storage. The lyophilized product is also more readily able to withstand the physical stresses of shipping. The reconstituted product is particle free, thus it can be administered without prior filtration.

The liquid formulation can be lyophilized using appropriate drying parameters. The following drying parameters are preferred: a primary drying phase temperature of about −20° C. to −50° C. and pressure between about 80 mTorr to about 120 mTorr; and a secondary drying phase at ambient temperature, and pressure between about 80 mTorr to 120 mTorr.

This lyophilized product retains the stability of immunological activity of the monoclonal antibody, and prevents the immunoglobulins intended for administration to human subjects from physical and chemical degradation in the final product.

The lyophilized product is rehydrated at the time of use in a diluent (e.g., sterile water or saline) to yield a particle-free solution. The reconstituted antibody solution is particle-free even after prolonged storage of the lyophilized cake at ambient temperature. The reconstituted solution is administered parenterally, preferably intravenously or subcutaneously, to the subject.

An important characteristic of the lyophilized product is the reconstitution time or the time taken to rehydrate the product. To enable very fast and complete rehydration, it is important to have a cake with a highly porous structure. The cake structure is a function of a number of parameters including the protein concentration, excipient type and concentration, and the process parameters of the lyophilization cycle. Generally the reconstitution time increases as the protein concentration increases, and thus, a short reconstitution time is an important goal in the development of high concentration lyophilized antibody formulations. A long reconstitution time can deteriorate the product quality due to the longer exposure of the protein to a more concentrated solution. In addition, at the user end, the product cannot be administered until the product is completely rehydrated. This is to ensure that the product is particulate-free, the correct dosage is administered, and its sterility is unaffected. Thus, quick rehydration offers more convenience to the patients and the physicians.

In lyophilized products, the desired dosage can be obtained by lyophilizing the formulation at the target protein concentration and reconstituting the product with the same volume as that of the starting fill volume. The desired dosage can also be obtained by lyophilizing a larger volume of a diluted formulation, and reconstituting it with a less volume. For example, if a desired product dosage is 100 mg of protein in 1 mL of the formulation, the formulations can be lyophilized with the following liquid configurations: 1 mL of 100 mg/mL, 2 mL of 50 mg/ml, or 4 mL of 25 mg/mL protein formulation. In all cases, the final product can be reconstituted with 1 mL diluent to obtain the target protein concentration of 100 mg/mL. However, as the protein concentration in the pre-lyophilized formulation is reduced, the fill volume increases proportionately. This correspondingly increases the length of the lyophilization cycle (especially the primary drying time), and thus significantly adds to the cost of the product. For example, if 1 mL fill volume (1 mm height in vial) of frozen material takes approximately 1 hour to sublimate its free water, then 10 mL fill volume (10 mm height) of frozen product will take approximately 10 hours of primary drying time. Therefore, it is advantageous to have a concentrated pre-lyophilized formulation (with antibody greater than 50 mg/mL) such that the lyophilization process will be more efficient.

The present invention provides a highly concentrated pre-lyophilized antibody formulation (greater than 50 mg/mL), which is lyophilized efficiently and effectively to a dry formulation that retains the biological, physical and chemical stability of the antibody. The dry formulation is stable for storage at least for 3 months, preferably 6 months, at room temperature. The dry formulation can be reconstituted within a short time of less than 2 minutes to a particle-free solution containing greater than 50 mg/mL antibody. Such highly concentrated antibody solution is ready for parenteral administration such as intravenous, intramuscular, intraperitoneal, or subcutaneous injection.

The invention is illustrated further by the following examples, which are not to be construed as limiting the invention in scope of the specific procedures described in them.

EXAMPLES

Example 1

Procedures of Lyophilization

Vial configuration: 2 mL fill in 5 mL Wheaton vial;
Lyophilization Cycle:
1. Freezing:
   Temp: −40° C.
   Rate: 2° C./min
   Freezing time: 3 hrs
2. Primary drying:
   Temp: −20° C.
   Rate: 1° C./min
   Duration: 12 hrs
   Pressure: 150 mTorr
3. Secondary drying:
   Temp: 20° C.
   Rate: 1° C./min Duration: 10 hrs
Pressure: 150 mTorr

Example 2

Preliminary Screening of Excipients

In this experiment, the formulation matrix contains 10 mg/ml anti-IL2 receptor antibody, 10 mM histidine, pH 6.0, and 0.015% Tween® 80. The excipients screened includes (a) cryoprotectors/lyoprotectors such as sucrose, trehalose, polyethylene glycol (PEG), and polyvinylpyrrolidone (PVP); (b) bulking agents and tonicity modifiers such as mannitol, glycine, and serine; and (c) Tg enhancers such as dextran.

Two mL of each formulation was filled into a vial, and lyophilized by a conservative lyophilization cycle according to Example 1. Each lyophile was reconstituted with 2 mL of sterile water.

Figure 1B:
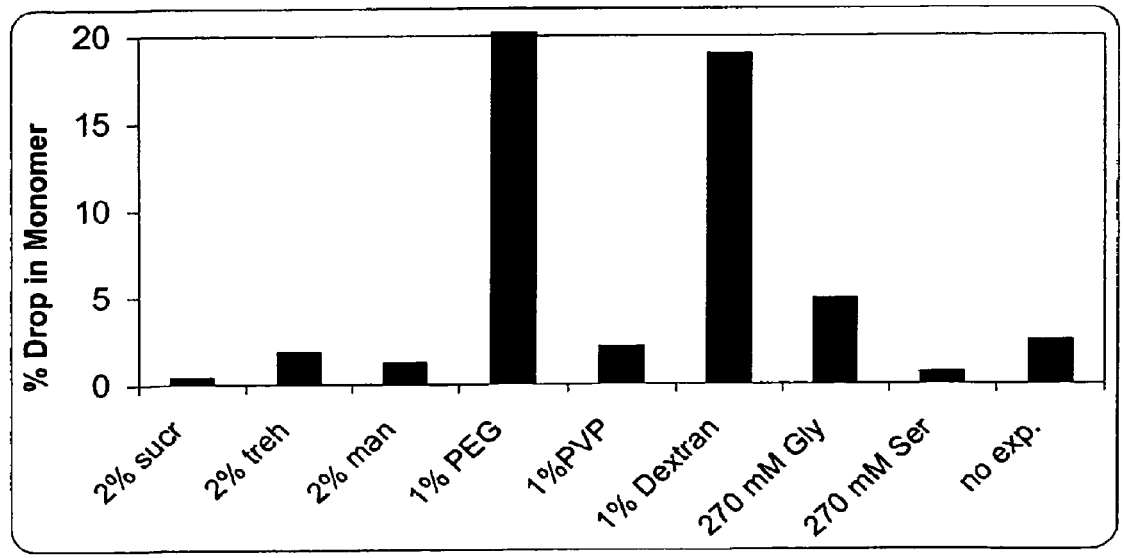

The accelerated stability test of each liquid formulation and each lyophile was performed at 55 or 40° C. The amounts of soluble aggregates was determined by SEC. The % monomer drop of different excipients was shown in FIG. 1.

The results indicated that PEG, dextran, and glycine decreased the pre-lyophilization liquid stability. The effect of all other excipients was comparable to the control formulation with no excipients.

The results also indicated PVP, dextran, and glycine caused significant protein aggregation in the lyophilized formulation. Relative to the control formulation, sucrose, mannitol and serine each stabilized the formulation against aggregation.

Example 3

Optimization of Sucrose, Mannitol and Serine Concentration

The effect of sucrose, mannitol and serine on the protein stability was investigated using an I-Optimal (Hardin-Sloane) experimental design approach.

In this experiment, the formulation matrix contains 50 mg/ml anti-IL2 receptor antibody, 10 mM histidine, pH 6.0, and 0.015% Tween® 180. The excipients screened include serine (0-100 mM), sucrose (0-120 mM) and mannitol (0-170 mM). The I-Optimal Design is shown as Table 1. Samples 1-15 are test formulations, and samples 16-20 are control formulations.

Two mL of each sample and control formulation was filled into a vial, and lyophilized according to the procedures described in Example 2. Each lyophile was reconstituted with 1 mL of sterile water. As the lyophile is reconstituted with only half the solution volume, osmolality and protein concentration are doubled.

TABLE 1

| | I-Optimal Design Table | | |
|---|---|---|---|
| Sample | Serine | Sucrose | Mannitol |
| 1 | 0.029 | −0.029 | −0.080 |
| 2 | 0.236 | 1.000 | 1.000 |
| 3 | 1.000 | 0.196 | 0.333 |
| 4 | 1.000 | −1.000 | 1.000 |
| 5 | −0.044 | 0.044 | −1.000 |
| 6 | −1.000 | 1.000 | 0.167 |
| 7 | 1.000 | 1.000 | −0.883 |
| 8 | −1.000 | −1.000 | −0.883 |
| 9 | −0.196 | −1.000 | 0.333 |
| 10 | 1.000 | −1.000 | −1.000 |
| 11 | −1.000 | −0.236 | 1.000 |
| 12 | −1.000 | 1.000 | −1.000 |
| 13 | 0.028 | −0.028 | −0.080 |
| 14 | 1.000 | −1.000 | 1.000 |
| 15 | −1.000 | 1.000 | −1.000 |
| 16 | −1.000 | 0.500 | −0.333 |
| 17 | 0.200 | 0.500 | −1.000 |
| 18 | −0.400 | 0.000 | −0.333 |
| 19 | 0.200 | −0.500 | −0.333 |
| 20 | −1.000 | −1.000 | −1.000 |

The lyophile product stability test was performed at 37° C. for 4 weeks. The formulations were distinguishable. The analytic methods of SEC and reconstitution time show statistically significant responses among the formulations.

Figure 2A:
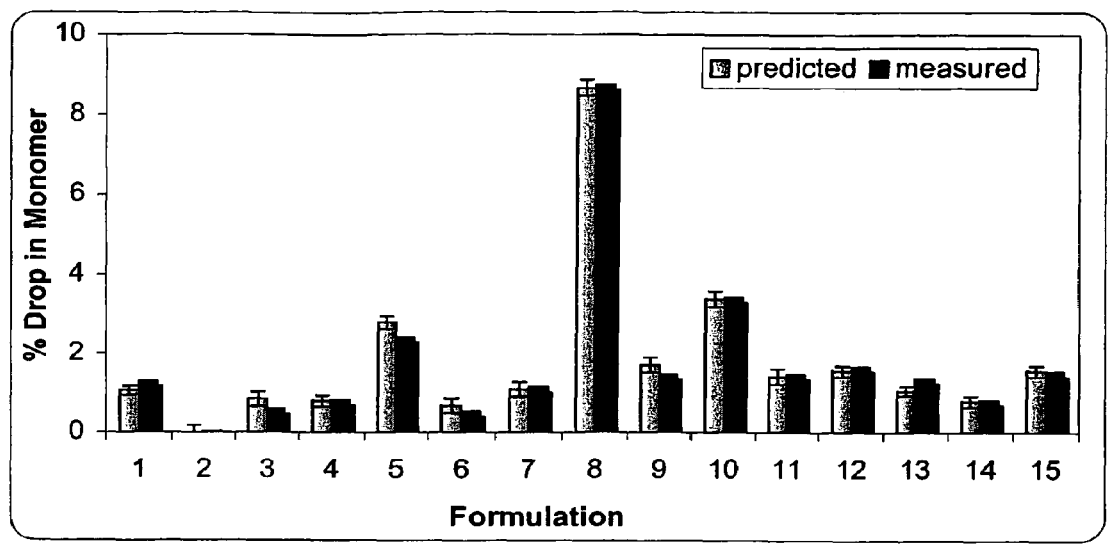
FIGS. 2A and 2B show the comparison of model predictions and experimental observation for the test samples 1-15.
Figure 2B:
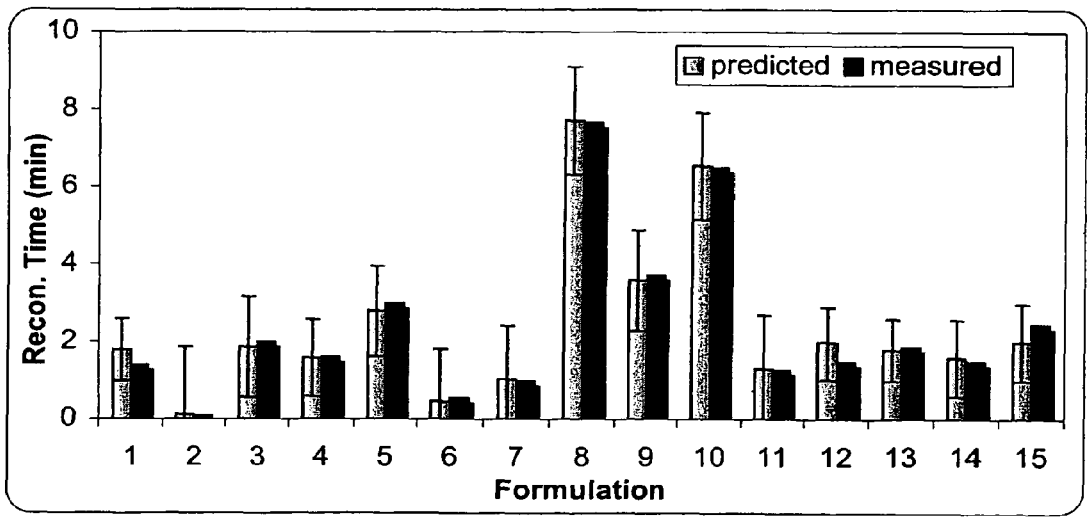
Figure 3A:
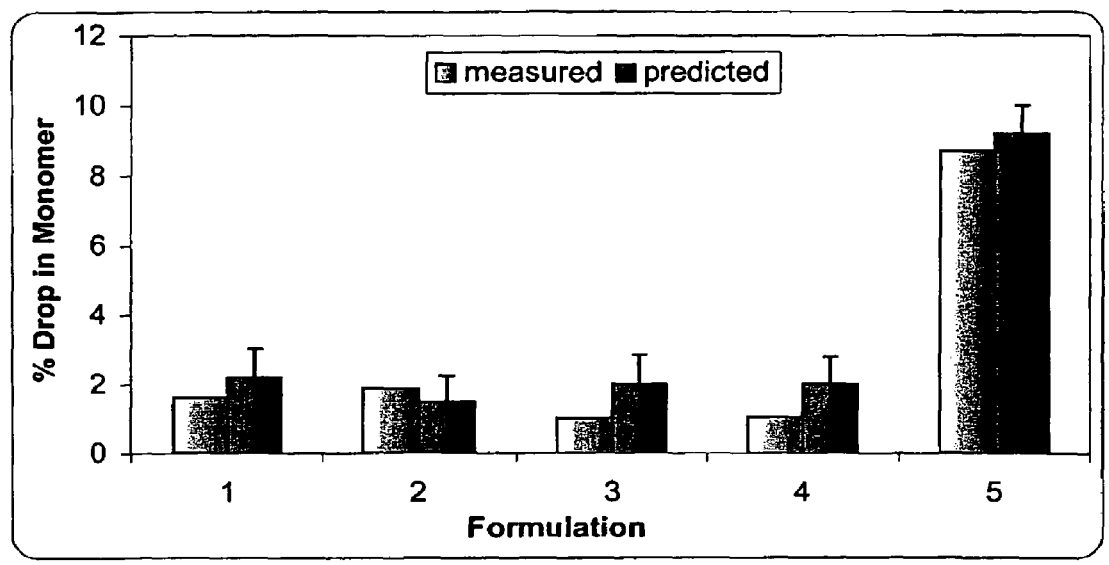
FIGS. 3A and 3B show the comparison of model predictions and experimental observation for the control samples 16-20.
Figure 3B:
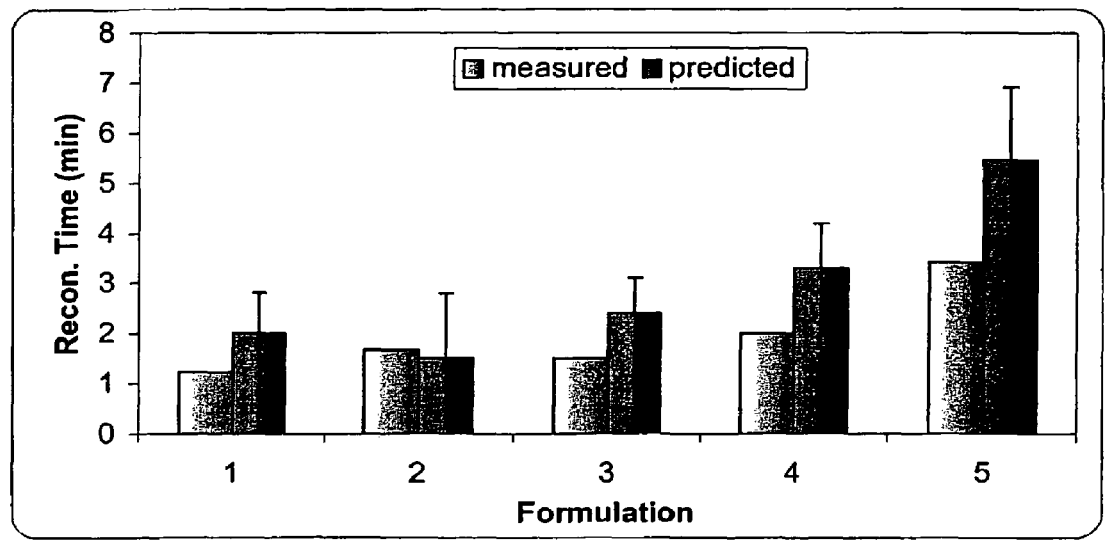
Figure 4A:
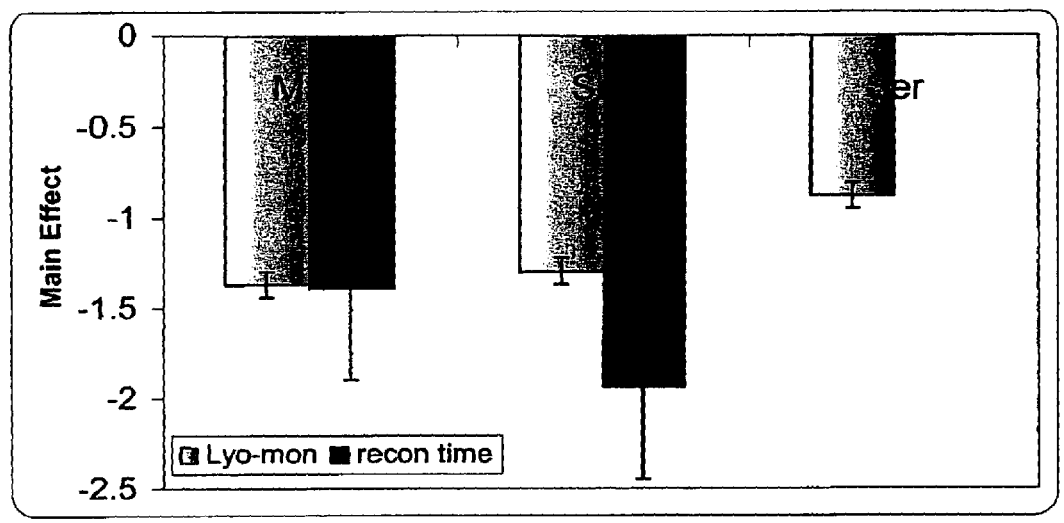
FIG. 4 shows the model coefficients of (A) main effect, and (B) interaction effect.
Figure 4B:
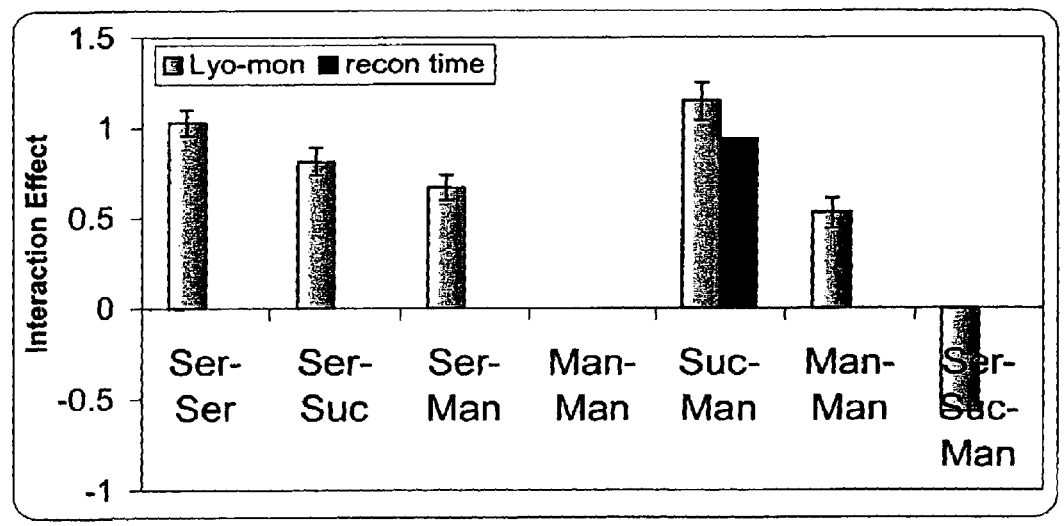

FIG. 2 shows the comparison of model predictions and experimental observation for the test samples. FIG. 3 shows the comparison of model predictions and experimental observation for the controls. FIG. 4 shows the model coefficients of main effect and interaction effect.

Figure 5B:
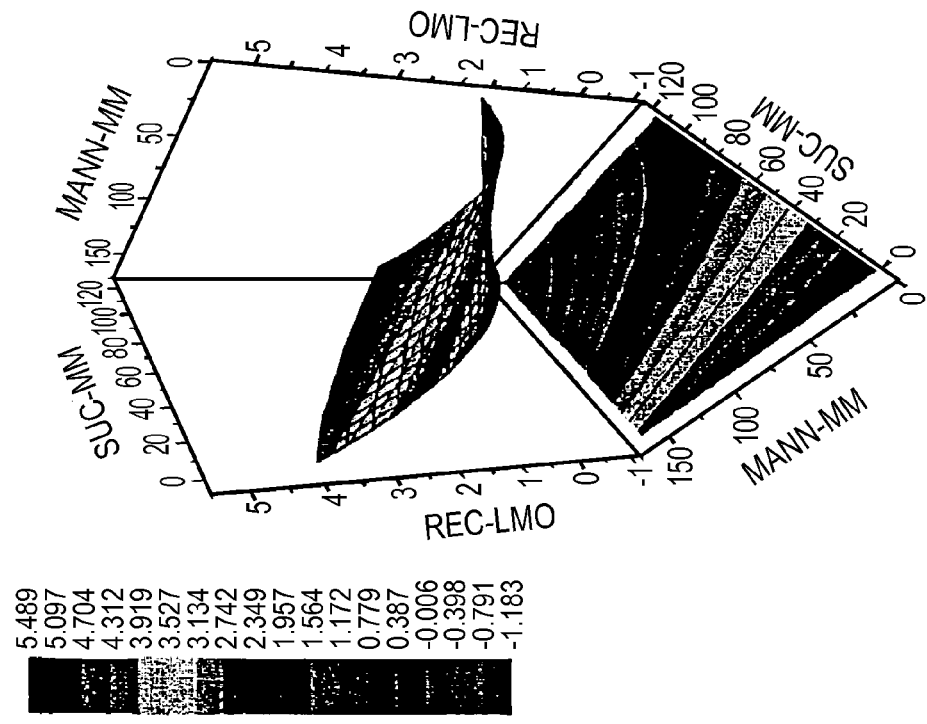
FIGS. 5A and 5B show the representative model simulations of mannitol vs. sucrose, [serine]=0.
Figure 5A:
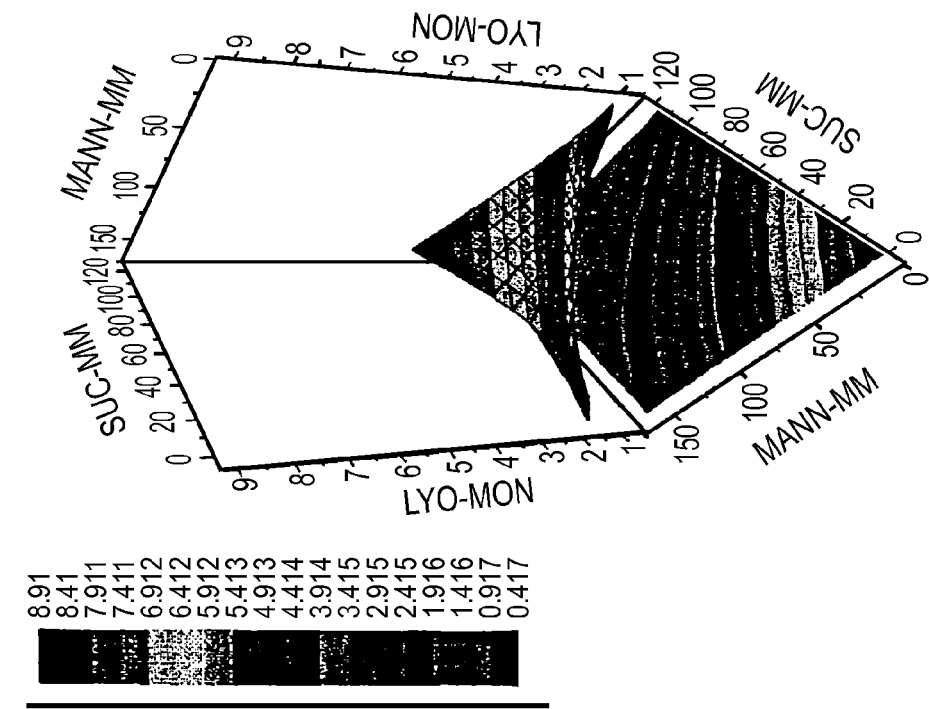

FIG. 5 shows the representative model simulations of mannitol vs. sucrose, [serine]=0. The results indicate that sucrose and mannitol stabilize the protein against aggregation (sucrose>mannitol). Sucrose has a favorable effect in reducing the reconstitution time. Using high concentrations of sucrose and mannitol, formulation stability is enhanced and cakes with short reconstitution time are obtained.

Figure 6B:
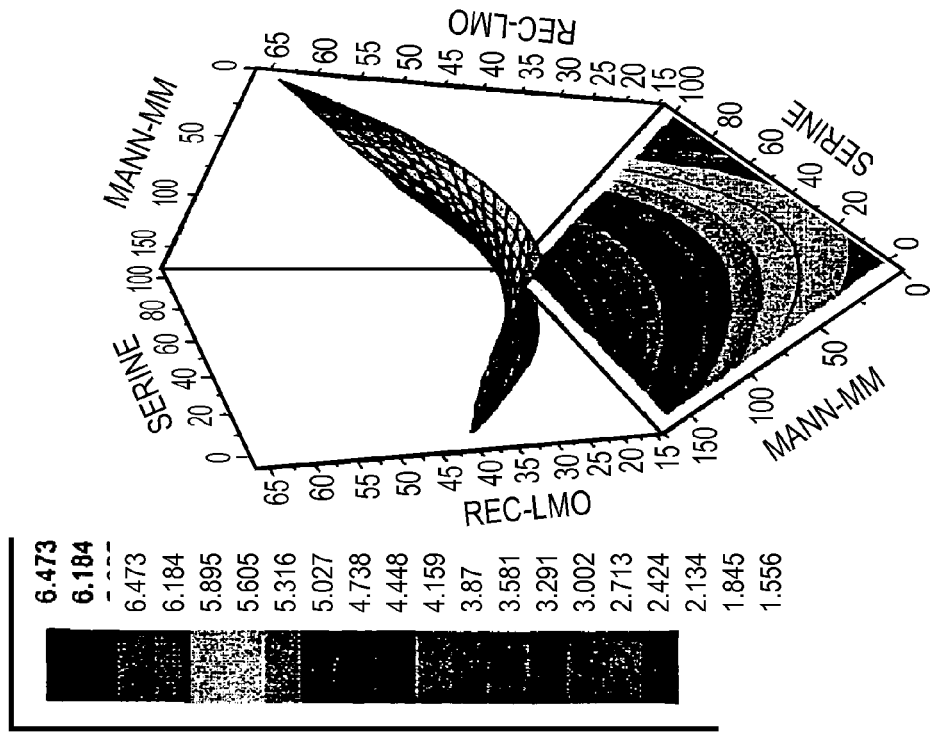
FIGS. 6A and 6B show the representative model simulations of mannitol vs. serine, [sucrose]=0.
Figure 6A:
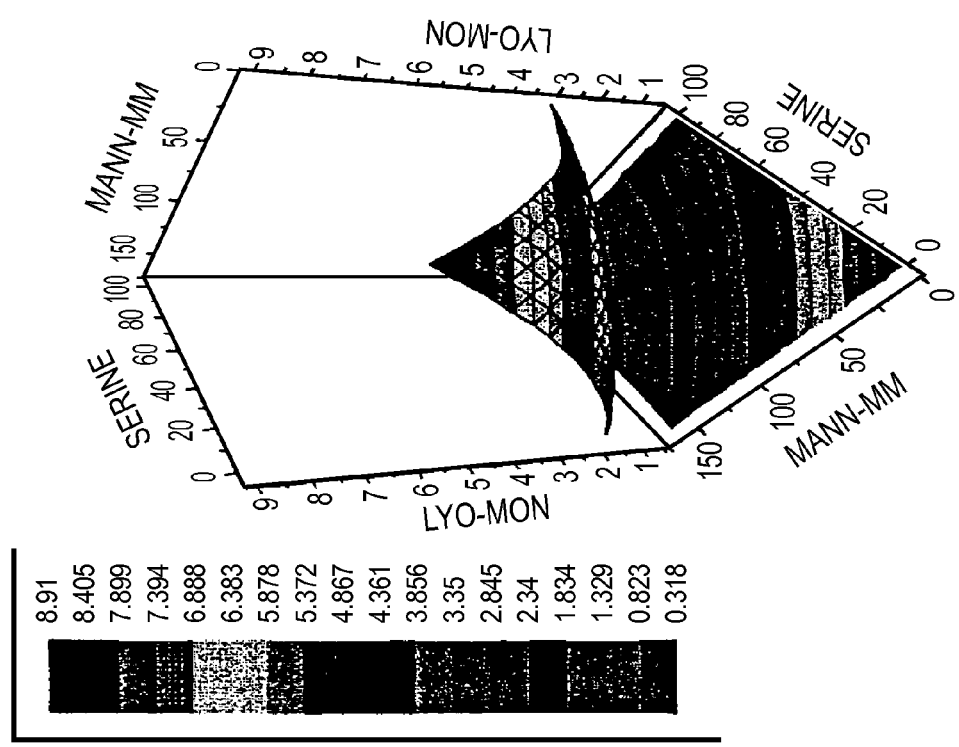

FIG. 6 shows the representative model simulations of mannitol vs. serine, [sucrose]=0. The results indicate that serine and mannitol stabilize the protein against aggregation (mannitol>serine). At high concentrations, serine increases the reconstitution time. Formulation stability is enhanced using high concentrations of serine and mannitol, and their combination significantly reduces the reconstitution time.

Figure 7B:
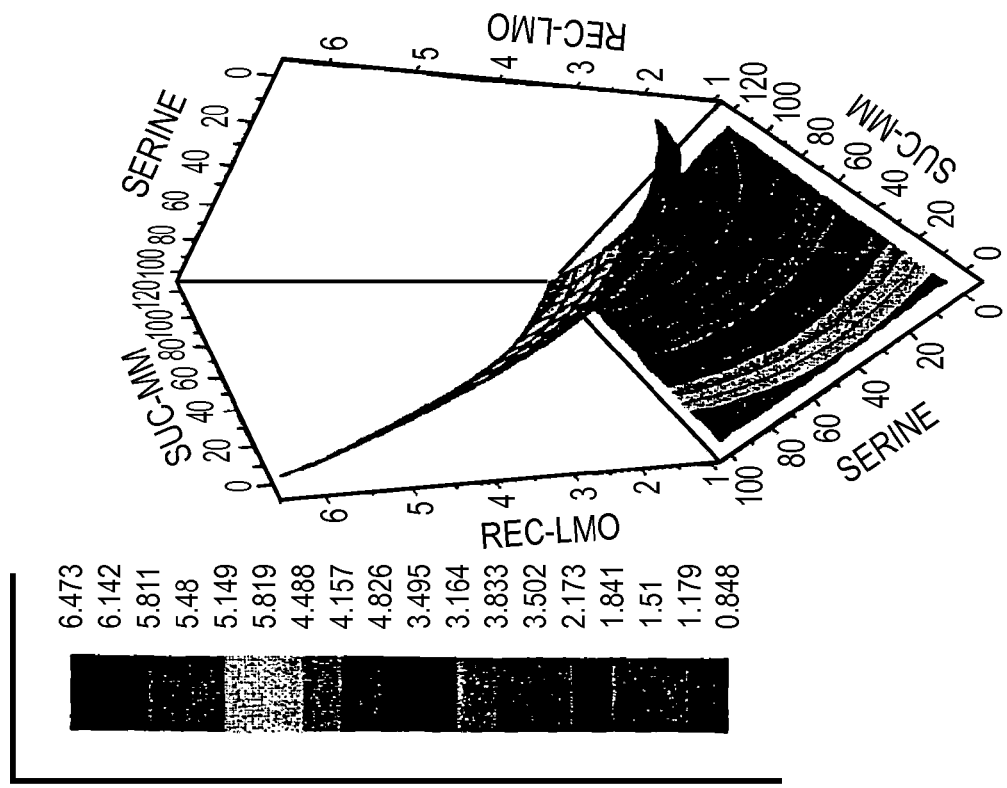
FIGS. 7A and 7B show the representative model simulations of sucrose vs. serine, [mannitol]=0.
Figure 7A:
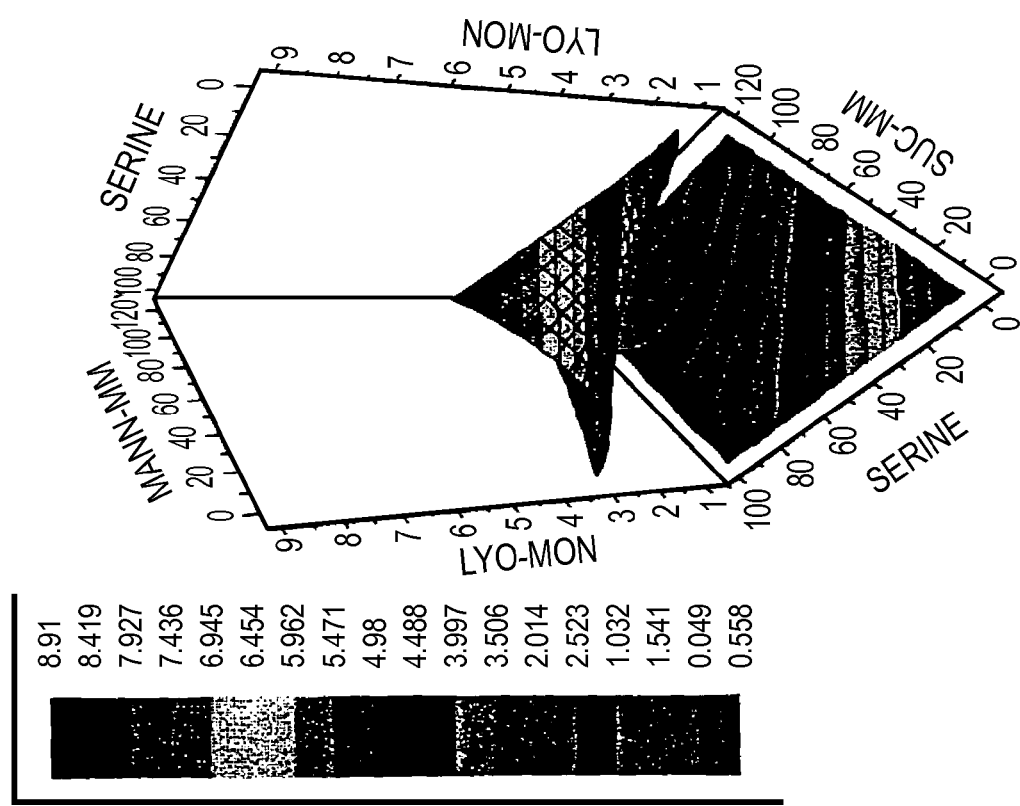

FIG. 7 shows the representative model simulations of sucrose vs. serine, [mannitol]=0. The results indicate that combinations of sucrose and serine can effectively stabilize the formulation against aggregation and form cakes with a short reconstitution time.

Figure 8B:
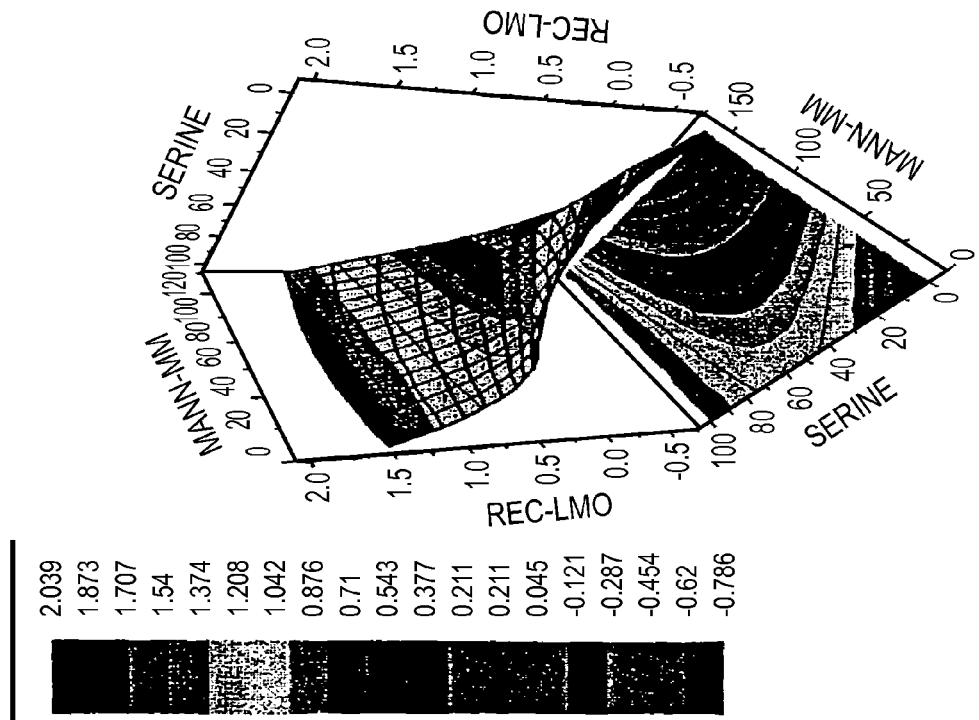
FIGS. 8A and 8B show the representative model simulations of mannitol vs. serine, [sucrose]=100 mM.
Figure 8A:
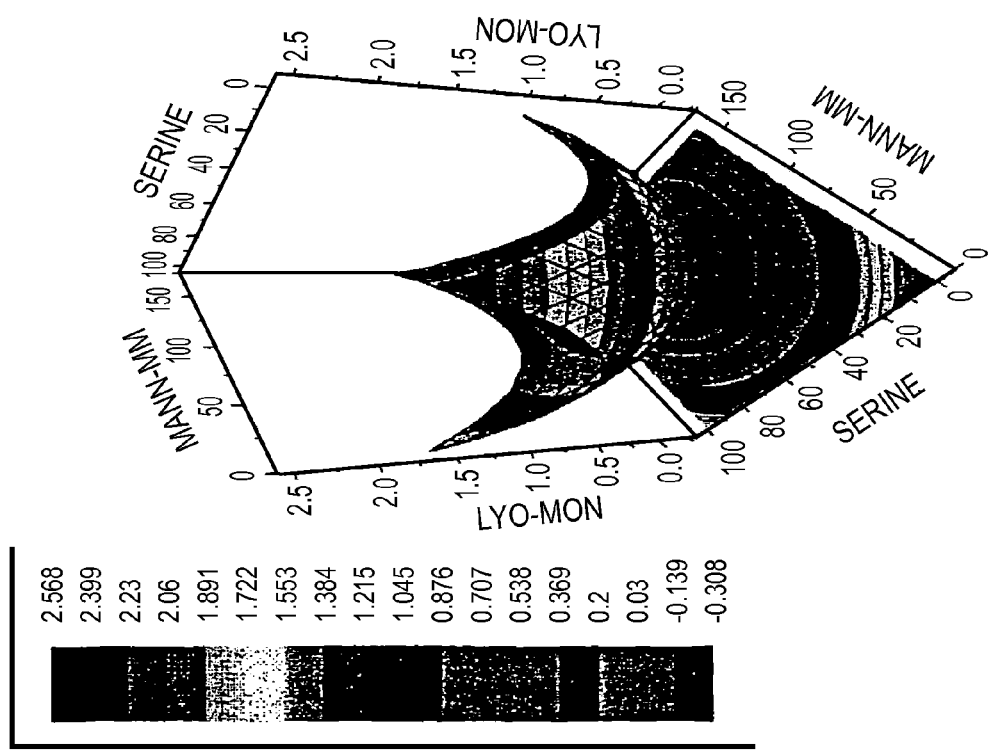

FIG. 8 shows the representative model simulations of mannitol vs. serine, [sucrose]=100 mM. Model simulations allow selection of conditions that provide isotonic formulations. Data supports maximizing the sucrose concentration. At 100 mM sucrose, the model provides conditions for optimizing serine and/or mannitol.

The conclusions for this experiment are as follows.

High concentrations of sucrose and mannitol provided maximum stability to the lyophilized formulation. However, osmolarity constraints precluded the addition of high concentrations of both excipients.

Sucrose had the strongest stabilizing effect on the lyophile stability, it also provides a cake with a short reconstitution time.

Example 4

Stability Data of Two Formulations

Formulations 1 and 2 were prepared and lyophilized according to procedures similar to those described in Example 1. The lyophilized formulation was incubated at 37°

C. for 2.5 months. The lyophilized formulation at different time point was reconstituted with 1 mL water and tested by analytical methods.

Formulation 1 (prior lyophilization): 50 mg/mL anti IL2 receptor antibody in 10 mM histidine buffer and 0.015% Tween® 80, pH=6, 25 mM Serine, 4% sucrose (117 mM), 0.25% Mannitol (13.7 mM)

|  | pH | Recon time (Seconds) | % Monomer | % Aggregates | Moisture (% w/w) |
|---|---|---|---|---|---|
| Pre-lyo | 6.1 | N/A | 98.1 | 1.1 | N/A |
| T0 | 6.1 | 40 | 98.2 | 0.9 | 0.75 |
| T = 2.5 mo | 6.1 | 36 | 97 | 1.9 | — |

Formulation 2 (prior lyophilization): 50 mg/mL drug in 10 mM histidine buffer and 0.015% Tween® 80, pH=6, 4% Sucrose (117 mM) and 0.5% Mannitol (27.4 mM)

|  | pH | Recon time (Seconds) | % Monomer | % Aggregates | Moisture (% w/w) |
|---|---|---|---|---|---|
| Pre-lyo | 6.1 | N/A | 98.1 | 1.1 | N/A |
| T0 | 6.0 | 32 | 98.2 | 1.0 | 0.8 |
| T = 2.5 months | 6.1 | 39 | 96.7 | 1.8 | — |

* The concentration of all excipients doubles after reconstitution of the cake with 1 mL water (half of the fill volume) for injection.
Pre-lyo: prior the lyophilization process
T0: The formulation has been lyophilized and immediately after this reconstituted with 1 mL water for injection
T = 2.5 months: The formulation was lyophilized; the cake was incubated at 37° C. for two and half months, then reconstituted with 1 mL water for injection (WFI).

Example 5

Long-Term Stability Study of Three Lyophilized Daclizumab Formulations

Study Description

Long-term stability of the following three formulations are tested at 5, 25 and 40° C. The stability of these samples is monitored over 24 months at To, 1 month, 3 months, 6 months, 12 months, and 24 months. The lyophilized formulation at different time point is reconstituted with water for injection (WFI) and tested by analytical methods.
1. Formulation I (FORM-I): 50 mg/mL anti-IL2 receptor antibody, 20 mM Histidine, 4% (117 mM) sucrose, 0.015% Tween® 80, pH 6.0. Vial configuration: 2 mL fill in 2 mL vial. Reconstituted with 1 mL WFI. Protein concentration post-reconstitution=100 mg/mL.
2. Formulation II (FORM-II): 80 mg/mL protein, 20 mM Histidine, 6.5% (190 mM) sucrose, 0.025% Tween 80, pH 6.0. Vial configuration: 1.25 mL fill in 2 mL vial, Reconstituted with 1 mL WFI. Protein concentration post-reconstitution=100 mg/mL.
3. Formulation III (FORM-III): 80 mg/mL protein, 20 mM Histidine, 4% sucrose, 0.015% Tween 80, pH 6.0. Vial configuration: 2 mL fill in 2 mL vial. Reconstituted with 1 mL WFI. Protein concentration post-reconstitution=160 mg/mL.

Summary of Results

Figure 9A:
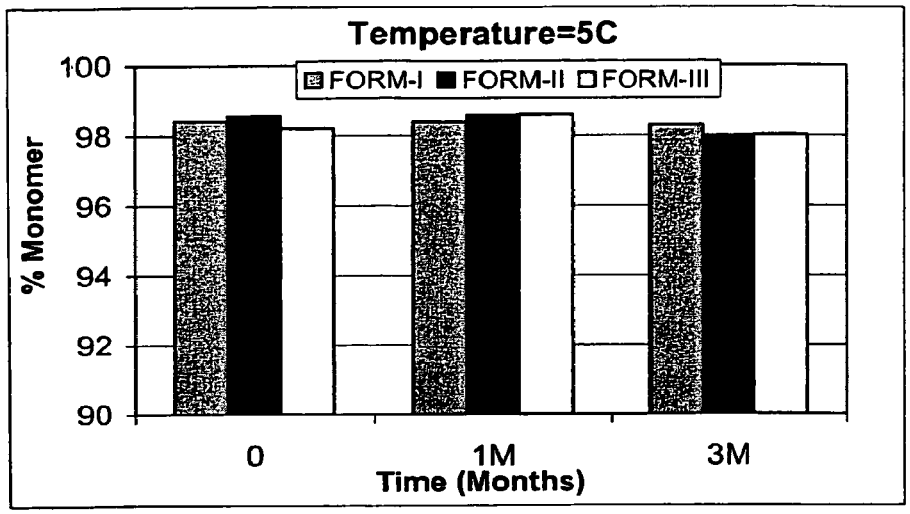
FIGS. 9A-9C show percent monomer in Formulations I, II and III as a function of time at (A) 5° C., (B) 25° C., and (C) 40° C.
Figure 9B:
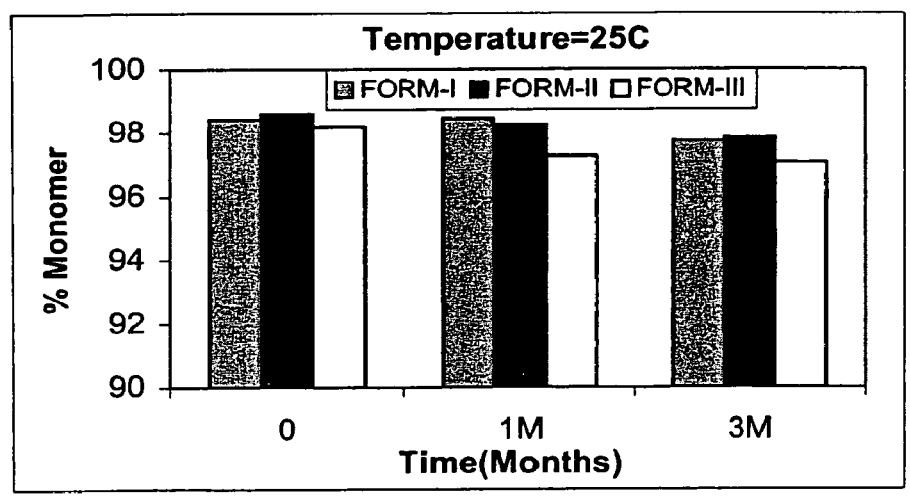
Figure 9C:
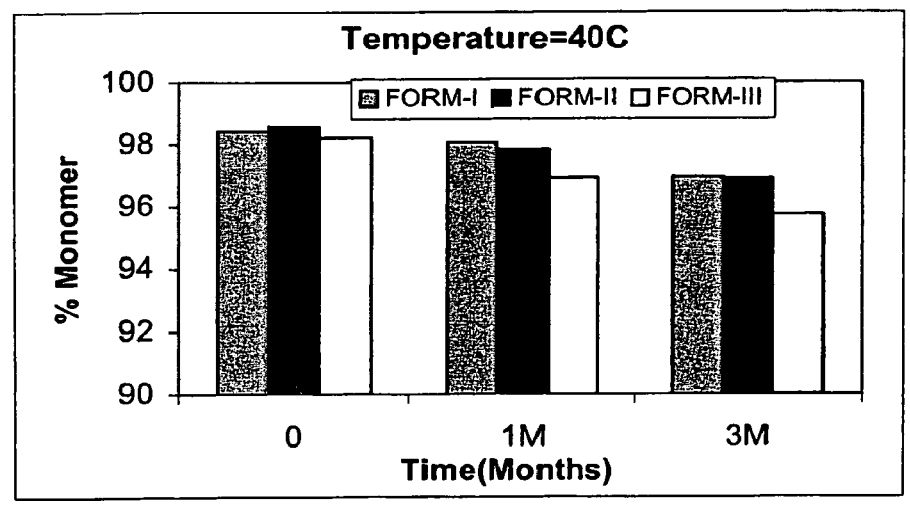

FIG. 9 shows the % monomer measured by size exclusion chromatography for the three formulations as a function of time and temperature. At 5° C., over the 3 month duration, no significant change is observed in the monomer content of the three formulations. At 25 and 40° C., over the 3 month duration, less than 3% drop in the monomer content is observed for all three formulations compared with To.

Figure 10A:
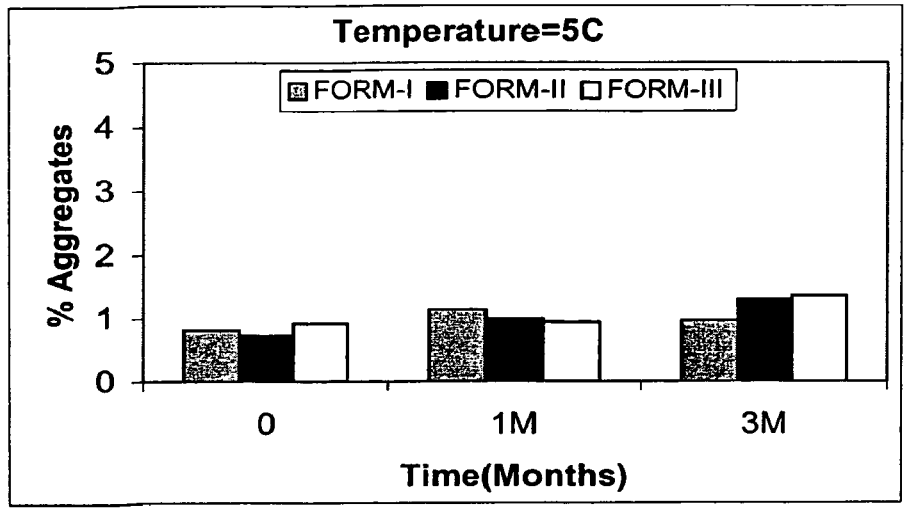
FIGS. 10A-C show percent aggregates in Formulations I, II and III as a function of time at (A) 5° C., (B) 25° C., and (C) 40° C.
Figure 10B:
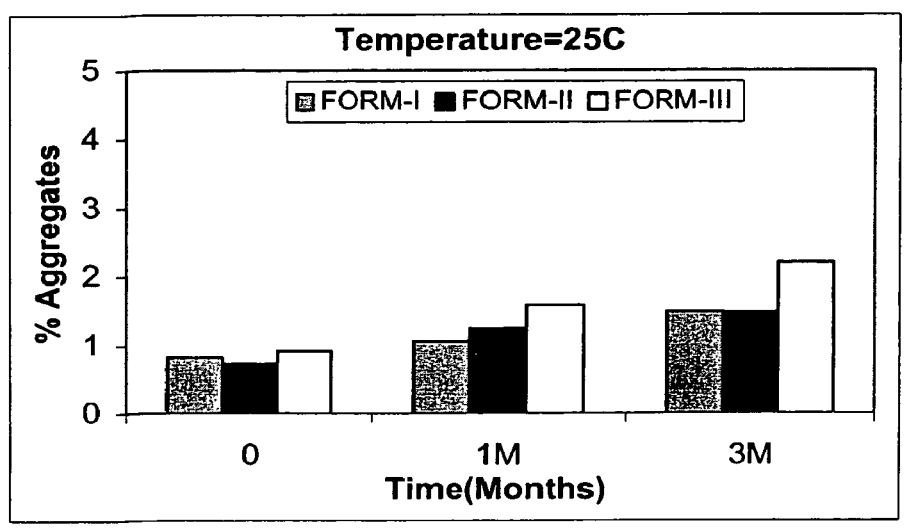
Figure 10C:
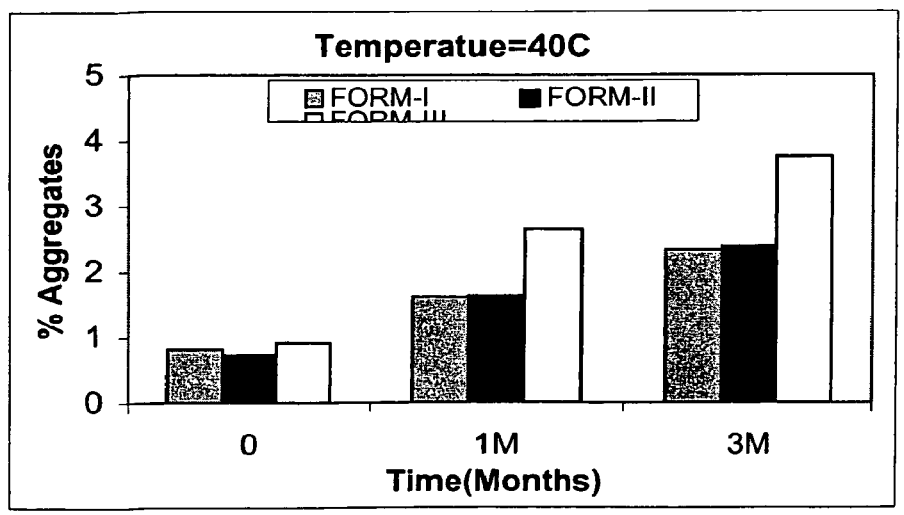

FIG. 10 shows the % aggregates measured by size exclusion chromatography for the three formulations as a function of time and temperature. No significant increase in aggregation is observed at 5° C. At 25° C. for 3 months, the increase in aggregation for FORM-I and FORM-II is <1% and ~2% for FORM-III. At 40° C. for 3 months, the increase in aggregation for FORM-I and FORM-II is about 2.5% and <4% for FORM-III.

Figure 11A:
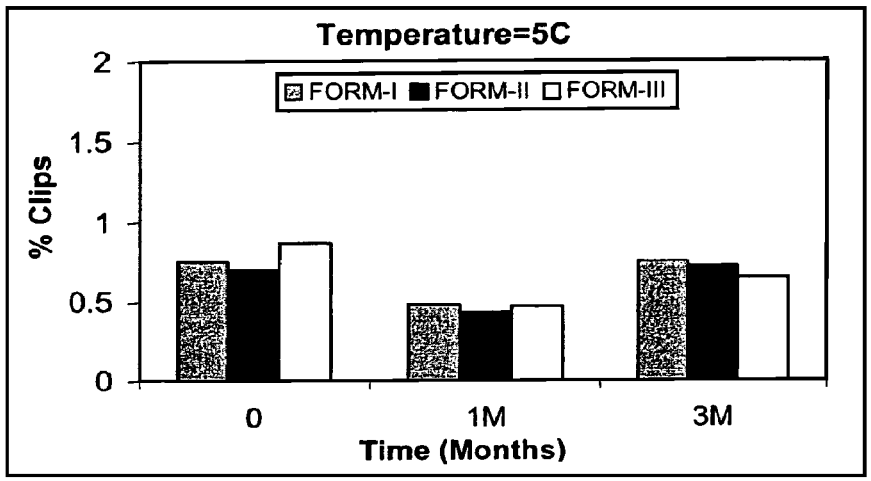
FIGS. 11A-C shows percent clips in Formulations I, II and III as a function of time at (A) 5° C., (B) 25° C., and (C) 40° C.
Figure 11B:
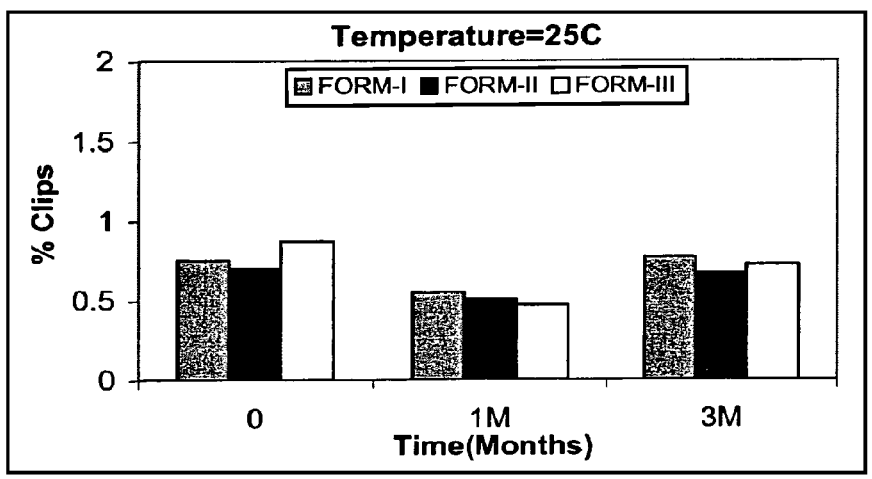
Figure 11C:
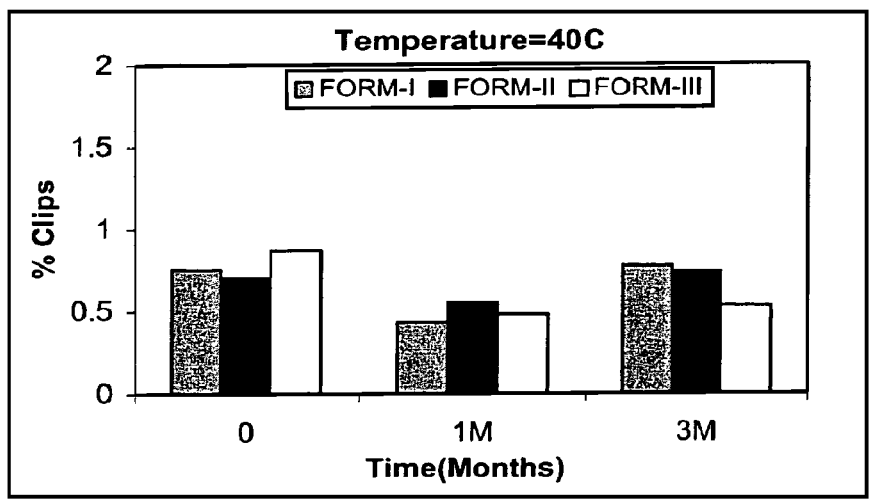

FIG. 11 shows the % clips measured by size exclusion chromatography for the three formulations as a function of time and temperature. Minimal changes in the % clips are observed for all three formulations over the three month duration at all temperatures. Thus, hydrolysis, which was a significant stability concern in the aqueous state, has been successfully curtailed in the lyophilized formulation.

In addition, the protein secondary structure in the lyophilized and the reconstituted formulations at the initial time point (T=0) and after 3 months at 40° C. is measured by Fourier Transform Infrared Spectroscopy (FTIR). For all formulations, no significant changes are observed in the secondary structure with time. Furthermore, the protein structure in the lyophilized and the reconstituted formulation appear unchanged. Generally, changes in the secondary structure between the lyophilized and the reconstituted liquid states, correlate with protein aggregation upon long-term storage.

The isoform profile of the three formulations at T=0 and T=3 months as a function of temperature is compared by cIEF analysis. For all formulations, minimal changes in the isoform profile are observed over the three month duration. Furthermore, no changes are seen as a function of temperature. Generally, isoform changes result due to chemical degradation processes such as deamidation and hydrolysis. This data is thus indicative of the chemical stability of the monitored formulations at temperatures as high as 40° C.

Table 2 lists the potency of the three formulations at T=0 and at T=3 months measured by an ELISA based binding assay. The bioactivity of the samples is preserved during the lyophilization cycle, and is unchanged upon storage for 3 months at temperatures as high as 40° C.

TABLE 2

| Sample | $T_0$ Pre-lyophilization | $T_0$ Reconstituted | 3 Months 5° C. | 3 Months 25° C. | 3 Months 40° C. |
|---|---|---|---|---|---|
| FORM-I | 99 | 89 | 84 | 76 | 80 |
| FORM-II | 99 | 94 | 81 | 83 | 77 |
| FORM-III | 95 | 96 | 78 | 78 | 80 |

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:
1. A method of reconstituting a lyophilized formulation, comprising adding a diluent to the lyophilized formulation to form a reconstituted solution, wherein the lyophilized formulation was prepared by lyophilizing an aqueous formulation comprising:

about 5-25 mM histidine buffer having a pH of from about 5.5 to about 6.5; about 0.005% to about 0.03% polysorbate;
about 100-300 mM sucrose; and
daclizumab;
which lyophilized formulation can, when diluent is added, be reconstituted to a solution containing 50-160 mg/ml daclizumab in a time of less than five minutes.

2. The method of claim 1, wherein the diluent is sterile, pyrogen-free water.

3. The method of claim 1, wherein the reconstituted solution is suitable for subcutaneous injection.

4. The method of claim 1, wherein the reconstituted solution in suitable for intravenous injection.

5. The method of claim 1, wherein the reconstituted solution is isotonic.

6. The method of claim 1, wherein the concentration of daclizumab before lyophilization is greater than 50 mg/ml and the concentration after daclizumab in the reconstituted solution is greater than 50 mg/ml.

7. The method of claim 1, wherein the time to form a particle-free reconstituted solution is less than five minutes.

8. The method of claim 7, wherein the concentration of daclizumab in the reconstituted solution is 160 mg/ml.

9. The method of claim 7, wherein the time to form a particle-free reconstituted solution is two minutes or less.

* * * * *